(12) United States Patent
Gutekunst (10) Patent No.: US 7,687,260 B2
(45) Date of Patent: *Mar. 30, 2010

(54) IMAGING FLUORESCENCE SIGNALS USING TELECENTRIC OPTICS

(75) Inventor: Martin Gutekunst, Eberfing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1089 days.

This patent is subject to a terminal disclaimer.

(21) Appl. No.: 11/333,617

(22) Filed: Jan. 17, 2006

(65) Prior Publication Data
US 2006/0166355 A1 Jul. 27, 2006

(30) Foreign Application Priority Data
Jan. 18, 2005 (EP) .................................. 05000862

(51) Int. Cl.
C12M 1/34 (2006.01)
C12M 3/00 (2006.01)

(52) U.S. Cl. ..................... 435/288.7; 435/6; 356/618

(58) Field of Classification Search .............. 250/458.1; 356/317; 435/288.7
See application file for complete search history.

(56) References Cited

U.S. PATENT DOCUMENTS

| | | | |
|---|---|---|---|
| 1,991,866 A * | 2/1935 | Rich | 362/520 |
| 5,118,801 A | 6/1992 | Lizardi et al. | |
| 5,538,848 A | 7/1996 | Livak et al. | |
| 6,246,525 B1 | 6/2001 | Ikami | |
| 6,498,690 B2 | 12/2002 | Ramm et al. | |
| 6,730,901 B1 | 5/2004 | Rushbrooke et al. | |
| 6,818,437 B1 * | 11/2004 | Gambini et al. | 435/288.7 |
| 2002/0003669 A1 | 1/2002 | Kedar et al. | |
| 2002/0005493 A1 | 1/2002 | Reese et al. | |
| 2002/0159057 A1 | 10/2002 | Odoy et al. | |
| 2003/0011772 A1 | 1/2003 | Abe et al. | |
| 2004/0009586 A1 * | 1/2004 | Oldham et al. | 435/287.2 |
| 2004/0038390 A1 * | 2/2004 | Boege et al. | 435/288.7 |
| 2004/0072335 A1 * | 4/2004 | Boege et al. | 435/287.2 |

FOREIGN PATENT DOCUMENTS

DE  3717274 A1  12/1988

(Continued)

OTHER PUBLICATIONS

Bernard, P. et al., "Integrated Amplification and Detection of the C677T Point Mutation in the Methylenetetrahydrofolate Reductase Gene by Fluorescence Resonance Energy Transfer and Probe Melting Curves," Analytical Biochemistry 255, 101-107 (1998) Article No. AB972427.

(Continued)

*Primary Examiner*—Walter D Griffin
*Assistant Examiner*—Shanta G Doe
(74) *Attorney, Agent, or Firm*—Dinsmore & Shohl LLP (57) ABSTRACT

The present invention relates to the field of DNA analysis. In particular, the present invention is directed to a device for the parallel imaging of fluorescence intensities at a plurality of sites as a measure for DNA hybridization. More particular, the present invention is directed to a device to image multiplex real time PCR or to read out DNA microarrays.

21 Claims, 2 Drawing Sheets

FOREIGN PATENT DOCUMENTS

| | | |
|---|---|---|
| DE | 19748211 A1 | 5/1999 |
| DE | 10131687 A1 | 1/2003 |
| DE | 10155142 A1 | 5/2003 |
| DE | 10200499 A1 | 7/2003 |
| EP | 0987540 A2 | 3/2000 |
| EP | 1136957 A1 | 9/2001 |
| EP | 1275954 A2 | 1/2003 |
| EP | 1 406 082 A1 | 4/2004 |
| EP | 1406082 A1 | 4/2004 |
| JP | 2002014044 | 1/2002 |
| JP | 2002014044 A | 1/2002 |
| JP | 2002357549 A | 12/2002 |
| JP | 2002543378 | 12/2002 |
| JP | 2003524754 T | 8/2003 |
| JP | 2005526254 | 9/2005 |
| WO | WO 97/46707 | 12/1997 |
| WO | WO 97/46712 | 12/1997 |
| WO | WO 97/46714 | 12/1997 |
| WO | 99/60381 | 11/1999 |
| WO | WO 99/60381 | 11/1999 |
| WO | 00/65325 | 11/2000 |
| WO | WO 02/14555 A2 | 2/2002 |
| WO | WO 03/069391 A1 | 8/2003 |
| WO | 03/098279 A2 | 11/2003 |

OTHER PUBLICATIONS

Matthews, J. et al., "Analytical Strategies for the Use of DNA Probes," Analytical Biochemistry 169, 1-25 (1988).

* cited by examiner

IMAGING FLUORESCENCE SIGNALS USING TELECENTRIC OPTICS

RELATED APPLICATIONS

This application claims priority to European patent application EP 05000862.2 filed Jan. 18, 2005.

FIELD OF THE INVENTION

The present invention relates to the field of DNA analysis. In particular, the present invention is directed to a device for the parallel imaging of fluorescence intensities at a plurality of sites.

BACKGROUND OF THE INVENTION

Various applications of fluorescence techniques to analyze biological samples are known to people skilled in the art. In case of electrophoretic techniques proteins or DNA are labeled with a fluorescence probe to visualize their electrophoretic bands in gels or columns. In addition, most biochip applications so far are based on a fluorescence read-out, whereas the specific binding of a fluorescence-labeled target molecule to a probe molecule immobilized on a solid support is monitored. Applications for DNA analysis in the liquid phase include fluorescence hybridization probes like the double-stranded DNA binding dye SybrGreenI or FRET (Fluorescent Resonance Energy Transfer) probes utilizing two fluorescence probes and energy transfer. A very important application for fluorescence techniques in the liquid phase is the quantification of PCR products in real time, the so-called real-time PCR.

In all these cases, a fluorescence reading device is needed that provides light of a certain wave length to excite the fluorescence label of the assay and that is able to detect the fluorescence light form said label emitted at a somewhat different wavelength. One major problem of all fluorescence reading devices is the enormous intensity of the excitation light in comparison with the fluorescence light emitted by the dye and therefore, one has to assure that the excitation beam does not hit the detector in order to monitor the fluorescence signals accurately. In other words, the optical path of the excitation light has to be different from the optical path of the fluorescence light, at least partially.

The realization of the fluorescence principle is quiet easy, when only one fluorescence probe has to be monitored in the liquid phase of e.g. a capillary. Here, e.g. a white light source together with a set of dichroic mirrors and filters is sufficient to meet the requirements. However, if more than one fluorescence label is present in the sample, a lateral distribution of spots on a solid support or the fluorescence of a microtiter plate has to be monitored, the requirements for the fluorescence reading device are more difficult to fulfill.

In principle, there are two different strategies to excite and monitor the fluorescence of a lateral distribution of sites. The first strategy is to scan the lateral distribution of sites, whereby the individual sites are successively analyzed one at a time. The second strategy is to illuminate the whole distribution of sites simultaneously and to image the corresponding fluorescence e.g. on a CCD chip. The scanning strategy has the obvious drawback that either the support has to be moved in two dimensions (WO 03/069391, DE 102 00 499) or the detector has to be moved with respect to the support (US 2002/159057). On the other hand, the main difficulty of the strategy to illuminate the whole support simultaneously is to assure a homogeneous illumination across the whole distribution of sites. An alternative to the homogeneous illumination of the whole distribution of sites is the use of an array of light sources, whereby each site is illuminated by its own light source. DE 101 31 687 describes this strategy for the evaluation of PCR in a thermocycler with a plurality of wells using a beam splitter and an array of LEDs for illumination. DE 101 55 142 describes the dark field monitoring of fluorescence signals, wherein the microarray is illuminated by an array of LEDs, too, but in this embodiment no beam splitter is needed.

Concerning the requirement to separate the optical path of the excitation beam and of the fluorescence light at least partially, there are again two different possibilities. The first possibility is the so called epi-illumination, whereby beam splitters are utilized and the excitation beam and the fluorescence light share at least part of the optical train. The second possibility is the use of oblique illumination. Here, the excitation beam is arranged in such a way that it has a certain angle to the normal of the support surface and the corresponding reflection of the excitation beam is outside of the acceptance angle of the detection system (e.g. US 2002/0005493 A1, EP 1 275 954 A2).

US 2003/0011772 A1 describes an optical apparatus to simultaneously observe a plurality of fluorescence dyes in a probe using a beam splitter. DE 197 48 211 A1 discloses a system to monitor the fluorescence signals generated in the wells of a microtiter plate simultaneously using a beam splitter, a field lens and an array of lenses focusing the light into each well. The detection is performed by imaging the light onto an array of photodiodes or a CCD chip. The fluorescence light collected in this embodiment of the system is appointed by the amount of dyes excited by the light cone of the focusing lens and therefore is dependent on the fill level of the well. WO 99/60381 claims an instrument for monitoring PCR reactions simultaneously in a plurality of vials in a temperature cycled block. The optical components of this instrument include again a beam splitter, a field lens, an array of vial lenses focusing individual light beams into each vial and a detection mean focusing the emission light onto e.g. a CCD detector. Due to the necessity of an array of vial lenses, the size and the lateral density of individual sites is limited. The JP 2002014044 describes a fluorometric apparatus to monitor fluorescence generated at a plurality of wells. The optical components comprise a beam splitter and a lens system to illuminate the wells collectively with light being parallel to the direction of the depth of the wells. However, the image forming optical system condenses the light onto a detection mean. U.S. Pat. No. 6,498,690 B1 discloses a method for imaging assays with an objective comprising a telecentric lens. U.S. Pat. No. 6,246,525 B1 claims an imaging device for imaging a sample carrier comprising a Fresnel lens.

Thus, it was the object of the present invention to provide an improved device for simultaneous monitoring of fluorescence signals from a lateral distribution of sites by optimizing the optical path towards homogeneous illumination and accurate detection. In one aspect of the present invention, the problem to be solved relates to improvements in monitoring multiplexed real-time PCR in a microtiter plate format.

SUMMARY OF THE INVENTION

Thus, the invention is directed to an optical instrument to image the fluorescence of an assembly of multiple individual sites, comprising a excitation across the whole assembly area as well as an accurate imaging of the corresponding fluorescence signals.

More precisely, the invention is directed to an optical instrument to analyze simultaneously a plurality of PCR amplifications taking place in the wells of a microtiter plate in real time or to image the fluorescence intensity of a microarray as a measure for specific target/probe interactions.

One subject matter of the present invention is an optical instrument for imaging fluorescence signals from multiple individual sites, comprising

- a holding means 1 for holding a planar support 2 with an assembly of multiple individual sites 3,
- at least one light source 4 emitting light comprising at least one excitation frequency,
- a transducer 5 disposed to be receptive of fluorescence signals from said assembly of multiple individual sites 3, whereas the transducer 5 is producing computable primary data,
- a field lens 6 transferring excitation light from said light source 4 to said assembly of multiple individual sites 3 and transferring fluorescence signals from said assembly of multiple individual sites 3 to said transducer 5,
- an excitation lens arrangement 10 transferring excitation light from said light source 4 to said field lens 6 and
- an imaging lens arrangement 11 transferring fluorescence signals from said field lens 6 to said transducer 5, whereas said excitation light and said imaging of fluorescence signals from multiple individual sites is telecentric on the object side of said field lens 6.

In the context of this invention an assembly of multiple individual sites summarizes objects that are composed of two or more sites being spacially separated and laterally distributed. Sites may be e.g. wells of a microtiter plate or functionalized surface areas of a glass slide. In the majority of cases the assembly of multiple individual sites will be arranged in a uniform manner and every site will have a different content in order to perform multiplexed analysis. Within the scope of this invention the planar support of the assembly is a planar solid phase. In case of a microarray, the planar support of the assembly is the surface of this planar solid phase, where the sites are arranged. In case of a microtiter plate, the planar support of the assembly is the plain, where the openings of the wells are arranged. The planar support of the assembly is fixated by a holding means in order to stabilize the position of each individual site at the desired position within the optical path.

Within the scope of this invention the phrase light source (LS) includes illuminants emitting light with a single frequency or with a plurality of different frequencies. Additionally, the light source may be an arrangement of more than one of said illuminants.

In the context of this invention a transducer (Det) is a device able to convert visible light into electrical signals that are processable by a computer, e.g. a CCD chip.

Within the scope of this invention a telecentric optic is an optic having a very small aperture and thus provides a high depth of focus. In other words, the telecentric light of a telecentric optic is quasi-parallel with the chief rays for all points across the object being parallel to the optical axis in object and/or image space. Therefore, the quality of an excitation optic or an imaging optic utilizing telecentricity in the object space is insensible to the distance of a certain object point to the optic. The aperture of a telecentric optic is imaged at infinity. In addition, using telecentric light a good lateral homogeneity across the light beam is assured and the sites located in the center of the assembly are comparable to those located at the boarder of the assembly. Throughout the present invention, a telecentric optic always comprises a field lens. In the context of this invention a field lens is a single lens that is closest to the objective that determines the field of view of the instrument, that comprise one or more components (achromat) and that contributes to the telecentricity in object and/or image space in combination with additional optical components of the apparatus.

The field lens of the present invention transfers excitation light from the light source to the assembly of multiple individual sites and transfers fluorescence signals from the assembly of multiple individual sites to the transducer. This does not exclude that additional optical components are introduced in the beam path e.g. between the light source and the field lens, between the field lens and the transducer or between the field lens and the assembly of multiple individual sites.

Another aspect of this invention is a real time PCR instrument comprising

- an optical instrument according to the invention and
- means for heating and cooling a support with one or more wells each containing a reaction mixture capable of performing a PCR reaction.

Within the scope of this invention the means for heating and cooling include any means capable of controlling and altering the temperature of the assembly of multiple individual sites in a cyclic manner in order to perform cyclic PCR amplification of nucleic acids. Preferably, the holding means can be heated and cooled being in thermal contact with the planar support of the assembly of multiple individual sites.

Yet another aspect of this invention is a system for imaging fluorescence signals of multiple assays, comprising

- a planar support 2 comprising an assembly of multiple individual assays,
- at least one light source 4 emitting light comprising at least one excitation frequency,
- a transducer 5 disposed to be receptive of fluorescence signals from said multiple assays, whereas the transducer is producing computable primary data and
- a beam path from said light source 4 to said transducer 5 that is characterized by a telecentric excitation of said assembly of multiple individual assays and by a telecentric imaging of said fluorescence signals generated at each individual assay of said assembly of multiple individual assays.

An assembly of multiple individual assays summarizes objects that are composed of two or more assays being spacially separated to realize a parallel analysis. These assays may be performed e.g. in wells of a microtiter plate or on functionalized surface areas of a glass slide.

The phrase beam path is used throughout this invention to summarize all areas the light beam traverses on its way from the light source through at least the field lens to the assembly of multiple individual assays and from the assembly of multiple individual assays through at least the field lens to the transducer.

Another subject matter of the present invention is a system to perform and to monitor a plurality of PCR reactions simultaneously in real time, comprising

- a multiwell plate with a plurality of individual sites each containing a reaction mixture capable of performing a PCR reaction;
- fluorescent DNA binding entities and
- a real time PCR instrument according to the invention, comprising an optical instrument according to the invention illuminating the whole multiwell plate with telecentric light and detecting the fluorescence signals from each well of said multiwell plate by a transducer disposed to be receptive of the corresponding fluorescence signals in order to produce computable primary data.

Throughout the present invention, the fluorescent DNA binding entities are all fluorescence dyes or assemblies of fluorescence dyes known to someone skilled in the art that may be used for the detection of amplified DNA, namely e.g. double-stranded DNA binding dyes, TagMan probes, molecular beacons, single label probes or FRET hybridization probes.

Yet another subject matter of the present invention is a method for amplifying, detecting and/or quantifying multiple target DNA sequences, comprising providing a composition or reaction mixture capable of performing PCR reactions, subjecting said reaction mixture to a thermocycling protocol such that amplification of said multiple target DNA sequences can take place and monitoring the presence and the amount of each DNA sequence at least once after a plurality of amplification cycles using fluorescent DNA binding entities and a real time PCR instrument according to the invention.

The composition or reaction mixture capable of performing PCR reactions comprises throughout this invention buffers, nucleotides, enzymes, primers and the fluorescence DNA binding entities.

A thermocycling protocol is the protocol defining the chronological temperature treatment of the PCR composition, the melting and annealing temperatures, the number of amplification cycles as well as the time for heating and cooling.

DETAILED DESCRIPTION OF THE INVENTION

One aspect of the invention is an optical instrument for imaging fluorescence signals from multiple individual sites, comprising:

a holding means 1 for holding a planar support 2 with an assembly of multiple individual sites 3, at least one light source 4 emitting light comprising at least one excitation frequency, a transducer 5 disposed to be receptive of fluorescence signals from said assembly of multiple individual sites 3, whereas the transducer 5 is producing computable primary data, a field lens 6 transferring excitation light from said light source 4 to said assembly of multiple individual sites 3 and transferring fluorescence signals from said assembly of multiple individual sites 3 to said transducer 5, an excitation lens arrangement 10 transferring excitation light from said light source 4 to said field lens 6 and an imaging lens arrangement 11 transferring fluorescence signals from said field lens 6 to said transducer 5, whereas said excitation light and said imaging of fluorescence signals from multiple individual sites is telecentric on the object side of said field lens 6.

There are a large number of instruments known to a person skilled in the art that are able to image fluorescence signals. If the optical instrument should be able to simultaneously image the fluorescence signals of an assembly of multiple individual sites, e.g. the wells of a microtiter plate or the spots of a microarray, one has to guarantee that the excitation of the dyes and the imaging of the fluorescence signals in the center of the assembly and at the boarder of the assembly are comparable. Moreover, even if the requirement of a homogeneous intensity distribution across the light beam is fulfilled, the alignment of the planar support is still of importance in order to assure that the support as a whole is in the focal plane of the imaging optic as well as of the excitation optic. Some particular problems arise in addition, when the support has depth, like in the case of microtiter plates.

A solution to the above mentioned problems is the use of telecentric optics. In a telecentric optic, the focal plane is located at infinity and the principal ray emanating from each object point is parallel to the optical axis. Consequently, all object points within a finite field of view are observed with the same perspective and the same intensity, in other words the telecentric optic has a large field depth and a homogeneous excitation or imaging profile.

A telecentric optic can be characterized by its numerical aperture (NA), which should be as small as possible to realize a high depth of focus:

$$NA = n \cdot \sin A,$$

whereas n is the refraction index of the medium and A the aperture angle. A high depth of focus is of utmost importance, if the assembly of individual sites has a certain depth, like in case of microtiter plates.

To design an optical instrument for telecentric excitation of a lateral distribution of sites and the telecentric imaging of fluorescence signals from said sites one has to take several aspects into consideration. From the aspect of the depth of focus alone, the NA value should be as small as possible. On the other hand, a small NA value for the imaging optic corresponds to a bad imaging resolution and a small NA value for the excitation optic corresponds to a waste of illumination power for excitation.

If the telecentric optical instrument should be applicable for a whole range of frequencies, the optic has to be achromatic, too. For the fluorescence imaging itself even more requirements have to be addressed, since the fluorescence imaging must have the right scaling for the correct reproduction of the lateral distribution of sites on the transducer. In addition, imaging errors like spherical or chromatic aberration, coma, astigmatism or curvature of field have to be controlled.

There are several ways to create telecentric optics. In general, a telecentric optic is a multi-element lens design, where more than one lens is arranged successively in the beam path. A telecentric optic can be prepared as telecentric in the object plane or as telecentric in the image plane or telecentric in both planes, a so-called doubly telecentric optic. Moreover, it is possible to illuminate an object with telecentric light and/or to monitor an object in a telecentric manner. In general it is enough to provide an optic with telecentricity in the object plain, since this guarantees already a homogeneous illumination of the whole object laterally as well as in the third dimension and the accurate collection of light irradiated from the object.

From the state of the art instruments are known that use telecentric optics for imaging fluorescence signals, but the excitation is usually performed in a non-telecentric manner e.g. by back illumination, oblique illumination or by an evanescent field. Throughout this invention, both the excitation of the multiple individual sites as well as the imaging of the fluorescence signals from the multiple individual sites is performed in a telecentric fashion.

Figure 1:
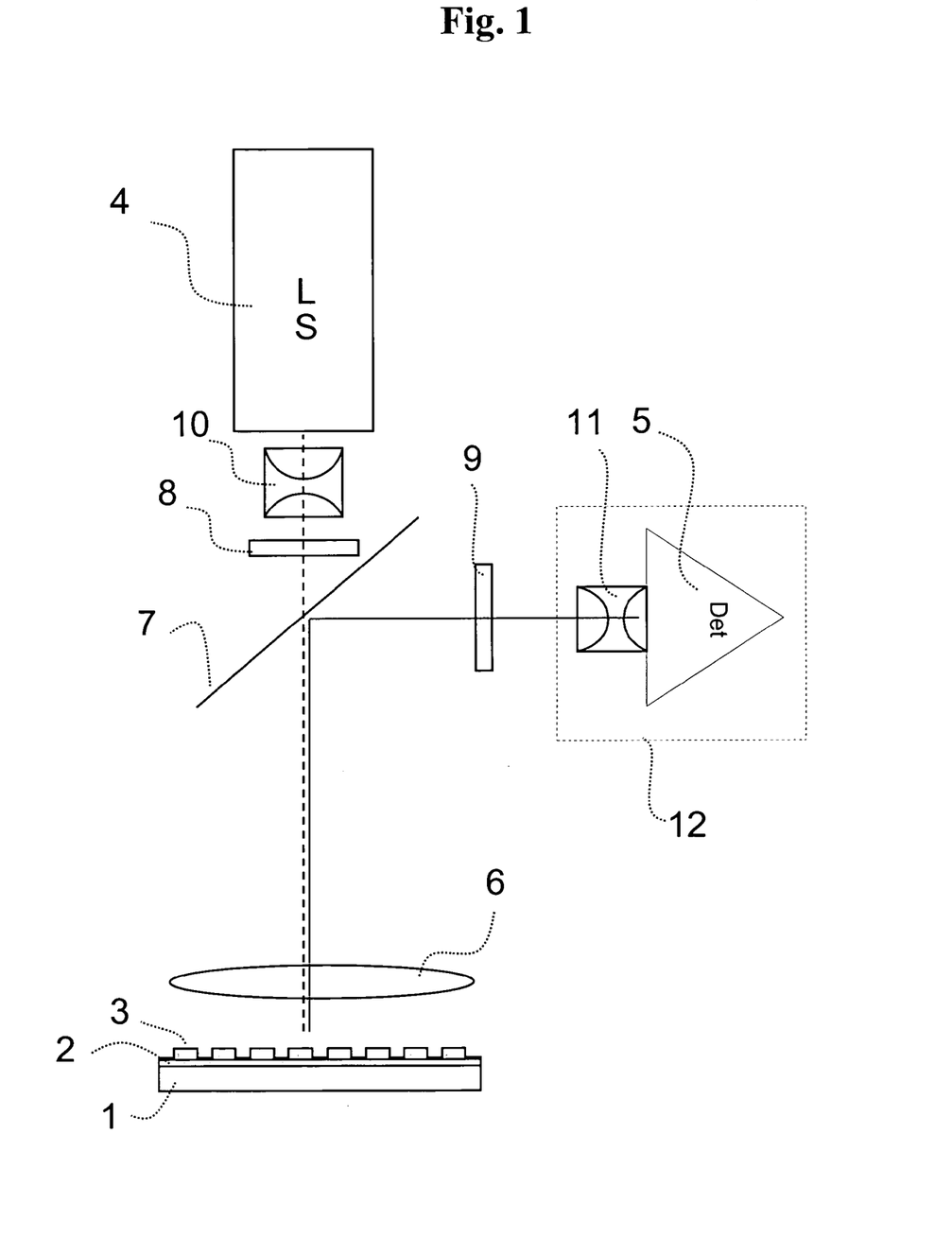
FIG. 1 Schematic picture of one embodiment of the optical instrument according to the invention.
Figure 2:
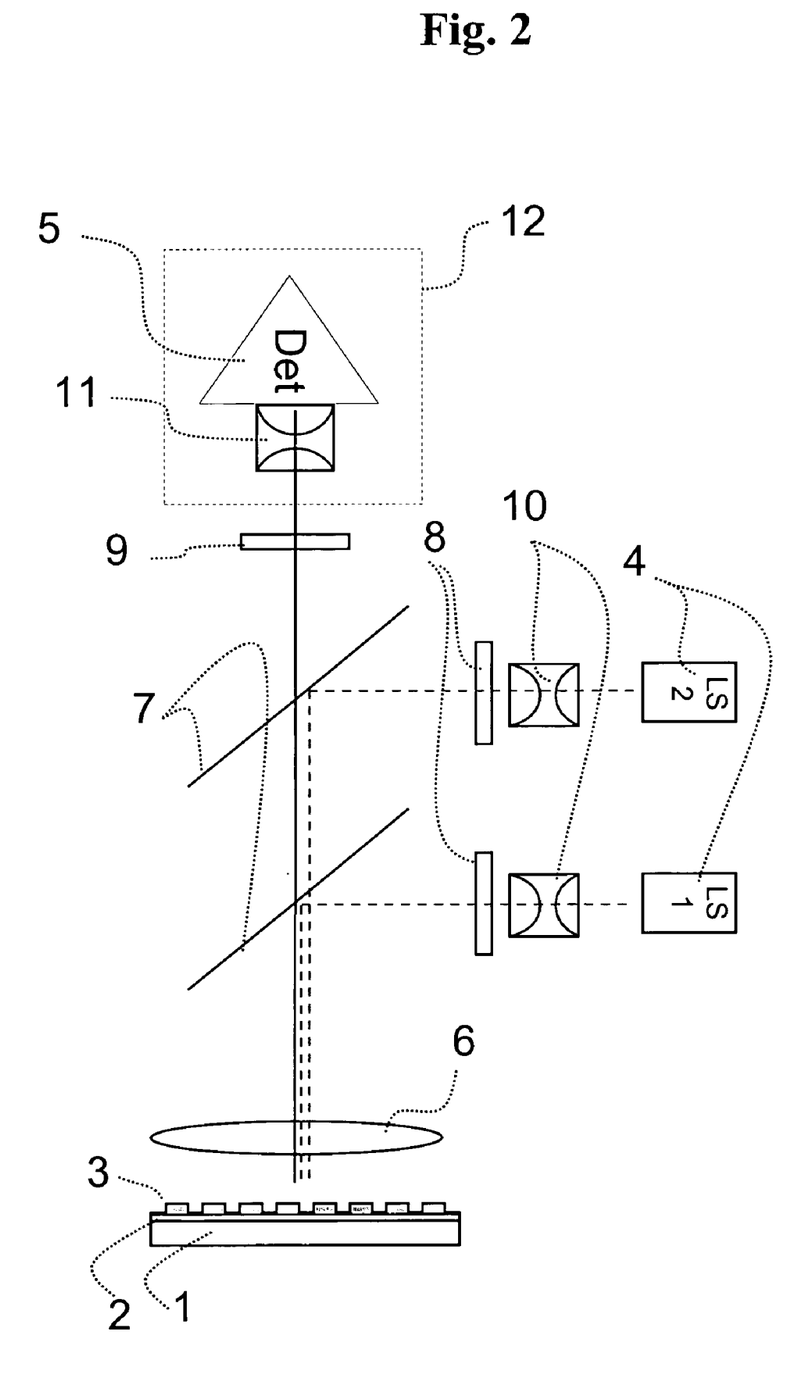
FIG. 2 Schematic picture of another embodiment of the optical instrument according to the invention.

FIG. 1 and FIG. 2 show schematic pictures of two optical instruments according to preferred embodiments of the invention that are explained in detail in the following.

A central part of all telecentric optics is the field lens. This lens is closest to the object and determines the diameter of the field of view of the instrument. Therefore, the diameter of this lens tends to grow in size, when the assembly of multiple individual sites is distributed over a large area. Field lenses exist as singlets (one single lens) or as achromats comprising e.g. two lenses pasted together. A special field lens that may be used for this invention is a Fresnel lens. A Fresnel lens has a special complex curvature with multiple tapered regions on at least one optical effective surface that provides the same telecentric properties as a field lens. In most cases, Fresnel lenses have only one surface with multiple tapered regions that is supported by a planar surface perpendicular to the optical axis and therefore, they are thinner in comparison to normal field lenses. In special cases, Fresnel lenses are provided that additionally have a curved supporting surface or that have multiple tapered regions on both sides of the lens. In addition, Fresnel lenses are sometimes made out of plastic and therefore, they can be cheaper than the large field lenses made out of glass. But on the other hand, the imaging quality, especially regarding contrast and cross-talk, of these Fresnel lenses is lower in comparison to normal field lenses, because of light scattering at those points of the lens with discontinuous curvature.

In a preferred embodiment, the optical instrument according to the invention further comprises a beam splitter 7 being transparent for at least one excitation frequency and reflective for the frequencies of said fluorescence signals or a beam splitter being reflective for at least one excitation frequency and transparent for the frequencies of said fluorescence signals.

A beam splitter is normally a dichroic mirror that passes or reflects light depending on its wavelength and therefore, it can be used to separate two components of a light beam into different directions in space. Such dichroic mirrors may be produced out of glass or plastic, if necessary with certain optically active coatings. They exist in form of thin foils or prisms.

For the application in an optical instrument to image fluorescence signals, this dichroic mirror must be reflective for the excitation light and transparent for the fluorescence light (FIG. 2) or the other way round (FIG. 1). The separation of the light emitted from the light source in a light beam containing the one or more excitation frequencies and a light beam with the other frequencies helps to secure that the fluorescence dyes are not destroyed by short wavelength and that undesired background irradiation by e.g. excitation of the support is reduced. The separation of the light from the multiple individual sites in a component containing the at least one excitation frequency from the component containing the fluorescence signals avoids that the reflexion of the excitation light with its high intensity hits the transducer. This improves the signal-to-noise ratio drastically.

In another further preferred variant of the invention, the field lens produces an excitation light beam being perpendicular to the support of the assembly of multiple individual sites.

The excitation light beam being perpendicular to the support of the assembly of multiple individual sites produces an reflection beam being perpendicular to the support of the assembly, too. But due to the beam splitter this reflection beam is separated from the fluorescence signals and does not hit the transducer. In case of e.g. a multititer plate as the assembly of multiple individual sites the perpendicular excitation light beam has the advantage that it is able to penetrate into the depth of the wells. On the other hand, if an excitation beam reaches the support with an angle of incidence larger than 0°, the walls of the wells would hinder the complete illumination of the well interior and only a fraction of the fluorescent dyes can be excited. Moreover, the amount of fluorescence dye excitation within the wells is depending on the filling level, when an oblique excitation beam is used.

In a further preferred variant, the optical instrument according to the invention further comprises an excitation filter system 8 capable of transferring at least one excitation frequency from said light source to said assembly of multiple individual sites, while blocking a plurality of other frequencies.

Such an additional excitation filter system can block certain frequencies from the light source even before the beam splitter. This may be necessary, if the light source comprises light of frequencies that can not be separated from the excitation frequencies by the beam splitter. A suitable excitation filter system is e.g. a so called filter wheel comprising a certain number of individual filters that have different optical properties. Using such a filter wheel provides a simple means to change the excitation frequencies. A special excitation filter system is e.g. a filter that adsorbs infrared (IR) frequencies or ultraviolet (UV) light. Such a special excitation filter system can be realized in form of a separate optical component, such as a thin film filter or in form of an optical active coating on other optical components of the apparatus.

In a further preferred embodiment, the optical instrument according to the invention further comprises a imaging filter system 9 capable of transferring the fluorescence signals from said assembly of multiple individual sites to said transducer, while blocking light with the excitation frequencies.

Such an additional imaging filter system can block certain frequencies generated at the multiple individual sites or from the excitation reflection yet after the beam splitter. This may be necessary, if light with frequencies that can not be separated from the excitation frequencies by the beam splitter are generated at the multiple individual sites. Again, a suitable imaging filter system is a filter wheel containing different filters. Analogous to the case of excitation filter system, a special imaging filter system can be for example an infrared (IR) filter or an ultraviolet (UV) filter. The special imaging filter systems can be realized in form of a separate optical component, such as a thin film filter or in form of an optical active coating on other optical components of the apparatus. Another imaging filter system is a filter system that avoids the detection of scattered light by the detector.

As mentioned before, the optical instrument according to the invention comprises an excitation lens arrangement 10, said excitation lens arrangement transferring light from said light source 4 to said field lens 6.

This means, the light from the light source is imaged on the assembly of multiple individual sites using an excitation optic comprising the field lens 6 and an excitation lens arrangement 10. Said excitation optic provides a telecentric excitation light on the object side of the field lens 6 and therefore is a telecentric excitation optic. The excitation lens arrangement comprises at least one lens, preferably at least three lenses in order to increase the aperture of the excitation towards better utilization of light source power. The excitation lens arrangement may comprise an asphere, if the amount of lenses should be reduced. Preferably, the telecentric excitation optic is designed to be achromatic in order to realize a homogeneous intensity distribution across the assembly of multiple individual sites independent from the excitation wavelength.

In another embodiment of the invention, said light source emits light comprising a plurality of frequencies, preferably said light source is a white light source, most preferably said light source is a gas discharge lamp, such as a Xenon lamp or a Mercury lamp or a filament lamp, such as a Tungsten lamp.

In yet another embodiment of the invention, said light source emits light with a single frequency, preferably said light source is a laser, most preferably said light source is a LED.

Using a light source emitting light with different frequencies has the advantage that this light source can be used for different fluorescence dyes only by changing the filter set composed of beam splitter and if necessary the excitation filter system and/or the imaging filter system. It is preferred to use filter wheels as excitation filter system and/or the imaging filter system containing a certain amount of filters in order to switch from one fluorescent dye to another easily. On the other hand, if the light source emits light with only a single frequency, the requirements for the filter set are easy to fulfill, but the optical instrument is fixed to a limited amount of fluorescence dyes.

In one embodiment of the invention, the light source window has an optical active coating that acts as a special excitation filter system to adsorb IR and/or UV light.

In a further preferred variant of the invention, said light source comprises a combination of more than one illuminant, preferably more than one laser, most preferably more than one LED.

In this preferred embodiment an assembly of different illuminants is used in order to provide an optical instrument according to the invention with more than one excitation frequency. One embodiment according to the invention with two different light sources is shown in FIG. 2, whereas each light source has its own excitation filter system 8, an excitation lens arrangement 10 and a beam splitter 7.

In another variant according to the invention, said light source further comprises a device to select one or more of said illuminants.

A device to select one of said illuminants can be realized in different ways. One possibility is to use turnable mirrors to inject the light of a selected illuminant into the optical path. Another possibility is to move the arrangement of illuminants in order to inject the light of a selected illuminant into the optical path.

The telecentric excitation optic according to the invention can comprise several additional components in addition to the field lens 6, the excitation filter system 8, the excitation lens arrangement 10 and the beam splitter 7. In one embodiment the telecentric excitation optic additionally comprises a light guide and light from the light source is coupled to said light guide in order to transfer the light from the light source to the optical components of the optical system. Using a light guide it is possible to couple light from different light sources and transfer this combined light simultaneously to the optical components. All kind of light guides are applicable for the purpose of the present invention. Possible light guides are for example fluid light guides, fiber light guides or bundles of fiber light guides. In an embodiment of the invention, one end or both ends of said light guide have an optical active coating that acts as a special excitation filter system to adsorb IR and/or UV light.

In yet another embodiment according to the invention, the telecentric excitation optic further comprises a light mixer to mix light from said light source and to image the illuminated surface of said light mixer onto the assembly of multiple individual sites.

A light mixer is a device with a very homogeneously illuminated surface that can be used as a light source providing light with a homogeneous intensity distribution throughout the whole cross-section. A light mixer is a longish entity made out of optical transparent material, whereas the boundaries of said entity are parallel to the optical path. In other words, a light mixer is a kind of optical fiber. Light that is injected into said light mixer experience multiple total reflections at the inner interface of the optical transparent material producing a cross-section area at the one end of the fiber that is very homogeneously illuminated. The total reflections at the inner interface of the optical transparent material is simply based on the change of refractive index at said interface or may be supported by reflective coatings. The ratio of the length of said light mixer to its cross section area is important for the illumination homogeneity. Said ratio is preferably larger than 2.

The light from the light source, particular from the cross-section area at the one end of the light mixer is imaged on the assembly of multiple individual sites using the telecentric excitation optic comprising the field lens 6 and an excitation lens arrangement 10. Therefore, in this embodiment of the invention the excitation of the multiple individual sites is performed with an excitation optic that is telecentric on the object site of the field lens 6.

The optical instrument according to the invention is adaptive to the imaging of chemiluminescence and bioluminescence, too. Since in these cases no excitation light is needed, the light source 4, the excitation lens arrangement 10 and the excitation filter system 8 can be omitted.

In a further preferred variant, the optical instrument according to the invention further comprises a light beam folding unit containing one, two or more folding mirrors, said folding unit folds light from said light source and fluorescence signals from said assembly of multiple individual sites.

Within the scope of this invention a light beam folding unit is a unit that provides a long optical path, while at the same time it only requires a confined amount of space. In order to adjust the numeric aperture from the excitation optic, one parameter that can be modified is the optical path the light has to traverse. Enlarging the optical path reduces the numerical aperture.

Therefore, if a small aperture is desired to fulfill the requirements field depth and homogeneous intensity distribution, the optical path will be long. Since large instruments are not eligible, the folding mirrors can be used to realize a long optical path and simultaneously confining the instrument size.

As mentioned before, the optical instrument according to the invention comprises an imaging lens arrangement 11, said imaging lens arrangement 11 transferring light from said field lens 6 to said transducer 5.

This means that the fluorescence signals generated at the assembly of multiple individual sites are imaged on a transducer 5 by a telecentric imaging optic comprising the field lens 6 and an imaging lens arrangement 11. In other embodiments of the invention, the telecentric imaging optic further comprises e.g. a light beam folding unit and/or special imaging filter systems 9.

The telecentric imaging optic has to be optimized on the size of the transducer and on the spacial size of the assembly of multiple individual sites. As in case of the excitation lens arrangement 10, the imaging lens arrangement 11 comprises at least one lens, preferably an assembly of at least 5 lenses. A large number of lenses are necessary for the imaging lens arrangement, since even higher requirements have to be addressed for the imaging optic compared to the excitation optic. The fluorescence imaging must have the right scaling for the correct reproduction of the lateral distribution of sites on the transducer. In addition, imaging errors like spherical or chromatic aberration, coma, astigmatism, special error or curvature of field have to be controlled. Due to the imaging of the fluorescence signals onto the transducer, the fluorescence imaging is performed with an imaging optic that is telecentric only on the object site of the field lens 6.

In a further preferred variant of the optical instrument according to the present invention, said imaging lens arrangement 11 is coupled to said transducer 5 forming an imaging unit 12.

Note that in this preferred embodiment of the present invention, the telecentric imaging optic is different to standard objectives, wherein all lenses are arranged and fixed in a defined manner forming the objective and said objective is placed as a whole in between the transducer and the object. Quite contrary, in this preferred embodiment of the present invention the imaging lens arrangement 11 is coupled to the transducer 5, forming a imaging unit 12. In order to fulfill the requirements concerning imaging resolution and accuracy, the positioning of imaging lens arrangement and transducer is of particular importance. In this embodiment, these requirements are met by optimizing the position between the imaging lens arrangement and the transducer before the optimized position is fixed. Said coupling between the imaging lens arrangement and the transducer is maintained throughout the intended use and is only released if a re-optimizing of the positioning becomes necessary.

In an embodiment of the optical instrument according to the invention, said transducer comprises a semiconductor device or preferably a charge coupled device.

In the context of this invention a transducer is a device able to convert light into electrical signals that are processable by a computer. This can be done by semiconductor devices having a band gap smaller than the energy corresponding to the fluorescence signals to be detected. The electrons generated in the conducting band of the semiconductor by illumination of the device produce a measurable signal that may be translated to computable data. Examples for these semiconductor devices are photodiodes or a charge coupled device (CCD).

A further preferred variant of the optical instrument according to the invention is an optical instrument, wherein the individual sites of said assembly are wells, the excitation light is parallel to the side walls of said wells and the solution filling said wells comprise fluorescent dyes.

An example for this further preferred variant of the optical instrument is a device for the simultaneous monitoring of PCR (polymerase chain reaction) amplifications taking place in the individual wells of a microtiter plate. The excitation light is parallel to the side walls of the wells in order to illuminate the whole interior of the wells independent from the filling height inside the wells. Since a telecentric optic for the excitation as well as for the fluorescence imaging is used, the results from a well in the center of the plate are comparable to those from wells at the boarder of the plate.

In case of PCR amplifications performed in individual wells, all fluorescence entities are applicable as fluorescent dyes that bind specifically to double-stranded nucleic acids. In the context of this invention these fluorescent dyes are named fluorescence DNA binding entities, whereas the fluorescence DNA binding entity is a molecule or a pair of molecules providing a characteristic fluorescence light, if they are bound to a double-stranded DNA. In the field of real-time PCR monitoring the following detection formats are known: DNA binding dye format (e.g. SybrGreenI), TaqMan probes, Molecular Beacons, Single Labeled Probe (SLP) format or FRET hybridization probes.

An also preferred embodiment of the optical instrument according to the invention is an optical instrument, wherein the individual sites of said assembly are spots on a planar support and the fluorescent dyes are attached to said spots.

An example for this preferred embodiment of the optical instrument is a device for the simultaneous imaging of fluorescence signals from different spots of a planar array. In a specific embodiment such an array is a DNA array, where lateral confined areas are functionalized with DNA probes having different sequences. In this case, the optical instrument according to the invention can monitor hybridization events with samples containing nucleic acids, if e.g. the complementary DNA strand is labeled with a fluorescence dye. Alternatively to the labeling of the DNA molecules in the sample, the hybridization events can be visualized by double-stranded nucleic acid binding fluorescent dyes, too.

The invention also concerns a real time PCR instrument comprising an optical instrument according to the invention and means for heating and cooling a support with one or more wells each containing a reaction mixture capable of performing a PCR reaction.

Within the scope of this invention, the means for heating and cooling include any means capable of controlling and altering the temperature of the assembly of multiple individual sites in a cyclic manner in order to perform cyclic PCR amplification of nucleic acids. Each PCR cycle comprises several different steps: an annealing step with decreasing temperature, an enzymatic amplification step at relatively low temperatures together with a detection step using fluorescent dyes and a melting step at high temperatures.

The invention further concerns a system for imaging fluorescence signals of multiple assays, comprising a planar support 2 comprising an assembly of multiple individual assays, at least one light source 4 emitting light comprising at least one excitation frequency, a transducer 5 disposed to be receptive of fluorescence signals from said multiple assays, whereas the transducer is producing computable primary data and a beam path from said light source 4 to said transducer 5 that is characterized by a telecentric excitation of said assembly of multiple individual assays and by a telecentric imaging of said fluorescence signals generated at each individual assay of said assembly of multiple individual assays.

An assembly of multiple individual assays summarizes objects that are composed of two or more assays being spacially separated to realize a parallel analysis. These assays may be performed e.g. in wells of a microtiter plate or on functionalized surface areas of a glass slide. In the majority of cases the assembly of multiple individual assays will be arranged in a uniform manner and every assay will have a different content in order to perform multiplexed analysis. In case of DNA microarrays each spot of the array is functionalized with an oligomer having a certain sequence, whereas in case of immunoassays each spot of the array is functionalized with e.g. proteins having different affinities. In case of microtiter plates in each well e.g. a different PCR is performed.

In a preferred embodiment of the system for imaging fluorescence signals of multiple assays according to the invention, said system further comprises a field lens, whereas said beam path passes said field lens twice.

In another preferred embodiment of the system for imaging fluorescence signals of multiple assays according to the invention, said system further comprises an imaging lens arrangement 11, whereas said imaging lens arrangement 11 is coupled to said transducer 5 forming an imaging unit 12.

In yet another preferred embodiment of the system for imaging fluorescence signals of multiple assays according to the invention, said system further comprises a beam splitter 7 being transparent for at least one excitation frequency and reflective for the frequencies of said fluorescence signals or a beam splitter 7 being reflective for at least one excitation frequency and transparent for the frequencies of said fluorescence signals.

A further preferred embodiment of the system for imaging fluorescence signals of multiple assays according to the invention further comprises an excitation filter system capable of transferring at least one excitation frequency from said light source to said assembly of multiple individual sites, while blocking a plurality of other frequencies and/or a imaging filter system capable of transferring the fluorescence signals from said assembly of multiple individual sites to said transducer, while blocking light with the excitation frequencies.

Another aspect of the invention concerns a system to perform and to monitor a plurality of PCR reactions simultaneously in real time, comprising
- a multiwell plate with a plurality of individual sites each containing a reaction mixture capable of performing a PCR reaction,
- fluorescent DNA binding entities and
- a real time PCR instrument comprising an optical instrument according to the invention illuminating the whole multiwell plate with telecentric light and detecting the fluorescence signals from each well of said multiwell plate by a transducer disposed to be receptive of the corresponding fluorescence signals in order to produce computable primary data.

In general, there exist different formats of fluorescent DNA binding entities for real time detection of amplified DNA, of which the following are well known and commonly used in the art:

a) DNA Binding Dye Format

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SybrGreen I, for example, do not affect the efficiency of the PCR reaction.

All other formats known in the art require the design of a fluorescent labeled Hybridization Probe which only emits fluorescence upon binding to its target nucleic acid.

b) TaqMan Probe

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. No. 5,538,848).

c) Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

d) Single Label Probe (SLP) Format

This detection format consists of a single oligonucleotide labeled with a single fluorescent dye at either the 5'- or 3'-end (WO 02/14555). Two different designs can be used for oligo labeling: G-Quenching Probes and Nitroindole-Dequenching probes.

In the G-Quenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe.

In the Nitroindole Dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

e) FRET hybridization Probes

The FRET Hybridization Probe test format is especially useful for all kinds of homogenous hybridization assays (Matthews, J. A., and Kricka, L. J., Anal. Biochem. 169 (1988) 1-25. It is characterized by a pair of two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

When annealed to the target sequence, the hybridization probes must sit very close to each other, in a head to tail arrangement. Usually, the gap between the labeled 3' end of the first probe and the labeled 5' end or the second probe is as small as possible, i.e. 1-5 bases. This allows for a close vicinity of the FRET donor compound and the FRET acceptor compound, which is typically 10-100 Angstroem.

Alternatively to monitoring the increase in fluorescence of the FRET acceptor component, it is also possible to monitor fluorescence decrease of the FRET donor component as a quantitative measurement of hybridization event.

In particular, the FRET Hybridization Probe format may be used in real time PCR, in order to detect the amplified target DNA. Among all detection formats known in the art of real time PCR, the FRET-Hybridization Probe format has been proven to be highly sensitive, exact and reliable (WO 97/46707; WO 97/46712; WO 97/46714). Yet, the design of appropriate FRET Hybridization Probe sequences may sometimes be limited by the special characteristics of the target nucleic acid sequence to be detected.

As an alternative to the usage of two FRET hybridization probes, it is also possible to use a fluorescent-labeled primer and only one labeled oligonucleotide probe (Bernard, P. S., et al., Anal. Biochem. 255 (1998) 101-107). In this regard, it may be chosen arbitrarily, whether the primer is labeled with the FRET donor or the FRET acceptor compound.

The invention further concerns a method for amplifying, detecting and/or quantifying multiple target DNA sequences, comprising provloading a composition or reaction mixture capable of performing PCR reactions, subjecting said reaction mixture to a thermocycling protocol such that amplification of said multiple target DNA sequences can take place and monitoring the presence and the amount of each DNA sequence at least once after a plurality of amplification cycles using fluorescent DNA binding entities and a real time PCR instrument according to the invention.

The following example, references and figures are provided to aid the understanding of the present invention, the true scope of which is set forth in the appended claims. It is understood that modifications can be made in the procedures set forth without departing from the spirit of the invention.

EXAMPLE

An optical instrument as explained in the detailed description and as illustrated in FIG. 2 (with only one light source) was configured as follows. The telecentric excitation optic was adjusted to handle frequencies from 450 to 650 nm and the telecentric imaging optic to handle frequencies from 500 to 740 nm. The light source was a Xenon lamp and as transducer a cooled ⅔" CCD chip with 1024×1344 pixels was used. The optical instrument was designed to image an area of 83 mm×117 mm so that microtiter plates (MTP) with 96 wells (distance 9 mm; diameter 5 mm) and 384 (distance 4.5 mm; diameter 3 mm) can be used. The appropriate wavelength for excitation and imaging for certain fluorescence dyes was adjusted by filter wheels.

The telecentric excitation optic had a numerical aperture on the side of the light source of 0.35 and on the side of the MTP of 0.014. The light source was arranged perpendicular to the CCD chip and the excitation light beam had to be oriented towards the MTP with a beam splitter reflective for the necessary excitation frequency and transparent for the other frequencies contained in the light from the light source. The excitation light beam from the beam splitter was perpendicular to the MTP and had an intensity variation across the object field (88 mm×122 mm) of below 10%. The imaging optic had an aperture on the object side of 0.014, too and a reproduction scale of −0.075 with an object-image distance of 800 mm. This large distance was realized with two folding mirrors. The imaging optic had a field depth of +/−3 mm. The used beam splitter was transparent for the fluorescence signals generated in the MTP wells due to excitation.

What is claimed is:

1. An optical instrument for imaging fluorescence signals from multiple individual sites, comprising:

a planar support with an assembly of the multiple individual sites;

a light source that emits light comprising an excitation frequency;

a field lens for transferring excitation light to an assembly of multiple individual sites positioned in said instrument, and for transferring fluorescence signals from said assembly of multiple individual sites to an imaging lens arrangement; wherein said imaging lens arrangement transfers fluorescence signals from said field lens to a transducer;

an excitation lens arrangement receiving light from said light source and transferring excitation light to said field lens; and wherein said transducer produces computable primary data from said fluorescence signals, wherein said excitation light and said fluorescence signals from the assembly of multiple individual sites are each telecentric on the object side of said field lens, and wherein said field lens is one single field lens arranged to be closest to the multiple individual sites.

2. An optical instrument according to claim 1 further comprising a beam splitter being transparent for an excitation frequency and reflective for the frequencies of said fluorescence signals.

3. An optical instrument according to claim 1 further comprising a beam splitter being reflective for an excitation frequency and transparent for the frequencies of said fluorescence signals.

4. An optical instrument according to claim 1 wherein said imaging lens arrangement is fixed to said transducer to form an imaging unit.

5. An optical instrument according to claim 1 wherein the assembly of individual sites comprises a plurality of wells that contain a solution comprising a fluorescent dye, and wherein the excitation light is transmitted parallel to the side walls of said wells.

6. An optical instrument according to claim 1 wherein said assembly of multiple individual sites comprises spots on said planar support, wherein fluorescent dyes are attached to said spots.

7. An optical instrument according to claim 1 further comprising a holding means for holding a planar support in a fixed position relative to the field lens, wherein said support comprises the assembly of multiple individual sites, provided on one surface of the support.

8. An optical instrument according to claim 1 wherein the assembly of individual sites comprises a plurality of wells, said instrument further comprising means for heating and cooling the contents of the plurality of wells.

9. A system for performing and monitoring a plurality of PCR reactions simultaneously in real time comprising:

a multiwell plate comprising a plurality of wells, wherein said wells comprise fluorescent DNA binding entities and a reaction mixture, said reaction mixture comprising components for conducting PCR;

means for heating and cooling said reaction mixture;

a light source that emits light comprising an excitation frequency;

a field lens that transfers excitation light to the multiwell plate, illuminating each well with telecentric light, and transfers fluorescence signals from each well of said multiwell plate to an imaging lens arrangement, and from the imaging lens arrangement to a transducer, allowing telecentric imaging of said fluorescence signals;

an excitation lens arrangement receiving light from said light source and transferring excitation light to said field lens; and wherein said transducer produces computable primary data from said fluorescence signals, and wherein said field lens is one single field lens arranged to be closest to said plurality of wells.

10. A system according to claim 9 wherein said imaging lens arrangement is fixed to said transducer to form an imaging unit.

11. A system according to claim 9 further comprising a beam splitter being transparent for an excitation frequency and reflective for the frequencies of said fluorescence signals.

12. A system according to claim 9 further comprising a beam splitter being reflective for an excitation frequency and transparent for the frequencies of said fluorescence signals.

13. A system according to claim 9 further comprising a holding means for holding said multiwell plate in a fixed position relative to the field lens.

14. A system for imaging fluorescence signals of multiple individual assays comprising:
- a planar support comprising an assembly of the multiple individual assays;
- a transducer which produces computable primary data based on fluorescence signals of the multiple individual assays;
- first and second light sources which each emit excitation light;
- an imaging lens arrangement which transfers the fluorescence signals to the transducer; and
- one single field lens arranged closest to the assembly of multiple individual assays to transfer excitation light emitted from the first and second light sources to the assembly of multiple individual assays and to transfer the fluorescence signals of the multiple individual assays to the imaging lens arrangement.

15. A system according to claim 14, wherein said imaging lens arrangement is fixed to said transducer forming an imaging unit.

16. A system according to claims 14 further comprising a beam splitter which reflects excitation light towards the one single field lens.

17. A system according to claims 14 further comprising a pair of beam splitters each associated with one of the light sources for reflecting excitation light towards the one single field lens.

18. A system according to claim 14 wherein the assembly of the multiple individual assays comprises fluorescent dyes spots on said planar support.

19. A system according to claims 14 further comprising an excitation lens arrangement which transfers excitation light from an associated one of the light sources.

20. A system according to claims 14 further comprising an excitation lens arrangement which transfers excitation light from one of the light sources, and an excitation filter system which transfers excitation light from the excitation lens arrangement.

21. A system according to claims 14 further comprising an imaging filter system situated between the one single field lens and the imaging lens arrangement.

* * * * *